(12) United States Patent
Ferreira Dos Santos Da Fonseca et al.

(10) Patent No.: US 11,484,256 B2
(45) Date of Patent: Nov. 1, 2022

(54) SYSTEMS AND METHODS FOR SLEEP STAGING

(71) Applicant: KONINKLIJKE PHILIPS N.V., Eindhoven (NL)

(72) Inventors: Pedro Miguel Ferreira Dos Santos Da Fonseca, Borgerhout (BE); Gregory Delano Matthews, Pittsburgh, PA (US); Michael Thomas Kane, Harrison City, PA (US); Mareike Klee, Straelen (DE); Raymond Charles Vasko, Jr., Turtle Creek, PA (US); Angela Grassi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 508 days.

(21) Appl. No.: 16/589,181

(22) Filed: Oct. 1, 2019

(65) Prior Publication Data
US 2020/0155060 A1    May 21, 2020

Related U.S. Application Data

(60) Provisional application No. 62/739,591, filed on Oct. 1, 2018.

(51) Int. Cl.
*A61B 5/00* (2006.01)
*A61M 16/00* (2006.01)
*A61B 5/085* (2006.01)
*A61B 5/087* (2006.01)
*A61B 5/091* (2006.01)

(52) U.S. Cl.
CPC ............ *A61B 5/4818* (2013.01); *A61B 5/085* (2013.01); *A61B 5/087* (2013.01); *A61B 5/091* (2013.01);

(Continued)

(58) Field of Classification Search
CPC .................................................. A61B 5/4818
See application file for complete search history.

(56) References Cited

U.S. PATENT DOCUMENTS 7,168,429 B2    1/2007  Matthews et al.
9,687,177 B2 *  6/2017  Ramanan ............. A61B 5/4812
(Continued)

FOREIGN PATENT DOCUMENTS

WO        2017132726 A1    8/2017

OTHER PUBLICATIONS

Fonseca P, Long X, Radha M, Haakma R, Aarts RM, Rolink J. Sleep stage classification with ECG and respiratory effort. Physiol Meas. 2015;36(10):2027-2040.
(Continued)

*Primary Examiner* — Travis R Hunnings (57) ABSTRACT

The present disclosure describes a sleep staging system. The system comprises: one or more sensors configured to generate output signals conveying information related to breathing parameters of subject during a respiratory therapy session; and one or more physical computer processors configured by computer readable instructions to: determine, based on the output signals, one or more breathing features of individual breaths of the subject; determine a distribution of the one or more breathing features over a plurality of time windows, at least one of the time windows having a length of at least 60 seconds; determine sleep states of the subject by mapping the distribution of the breathing features to one or more sleep states using a sleep stage classifier model, the sleep stage classifier model configured to determine the sleep states; and provide feedback indicating the sleep states during the respiratory sleep session.

23 Claims, 8 Drawing Sheets

(52) U.S. Cl.
CPC ............ *A61B 5/486* (2013.01); *A61B 5/4812* (2013.01); *A61B 5/7264* (2013.01); *A61M 16/024* (2017.08); *A61M 16/026* (2017.08); *A61M 2230/40* (2013.01)

(56) References Cited

U.S. PATENT DOCUMENTS

| | | |
|---|---|---|
| 2006/0111635 A1 | 5/2006 | Todros |
| 2006/0169282 A1 | 8/2006 | Izumi |
| 2014/0088373 A1 | 3/2014 | Phillips et al. |
| 2014/0213937 A1 | 7/2014 | Bianchi et al. |
| 2015/0119741 A1 | 4/2015 | Zigel et al. |
| 2017/0258365 A1 | 9/2017 | Ramanan |
| 2017/0360308 A1 | 12/2017 | Fonseca et al. |
| 2019/0178980 A1* | 6/2019 | Zhang .................... G01S 7/415 |
| 2020/0108215 A1* | 4/2020 | Nakai .................... A61B 5/087 |

OTHER PUBLICATIONS

Beattie Z, Oyang Y, Statan A, et al. Estimation of sleep stages in a healthy adult population from optical plethysmography and accelerometer signals. Physiol Meas. 2017;38:1968-1979.

Fonseca P, Weysen T, Goelema MS, et al. Validation of photoplethysmographybased sleep staging compared with polysomnography in healthy middle aged adults. Sleep.2017;40(7).

Zhang, Li et al., "Sleep stages classification CW Doppler radar using bagged trees algorithm", 2017 IEEE Radar Conference.

\* cited by examiner

SYSTEMS AND METHODS FOR SLEEP STAGING

CROSS-REFERENCE TO PRIOR APPLICATIONS

The present application claims the benefit of priority to U.S. provisional application Ser. No. 62/739,591, filed Oct. 1, 2018, the entity of which is incorporated herein by reference for all its disclosure and teachings.

BACKGROUND

1. Field

The present disclosure pertains to systems and methods for sleep staging.

2. Description of the Related Art

The present disclosure relates to systems and methods for determining sleep stages. The disclosure, in one embodiment, incorporates the system and methodology into systems that can also be used to detect or treat breathing disorders. Obstructive Sleep Apnea (OSA) is a common form of sleep-disordered breathing (SDB). Continuous Positive Airway Pressure (CPAP) is usually a medical therapy for treatment of OSA. Currently, CPAP machines provide a feedback to the patient, that it is mainly focused on parameters related to the therapy itself, (treated) apnea-hypopnea index (AHI), usage history, leaks, etc. However, CPAP systems that provide effective feedback regarding the effect of therapy on the objective measured sleep quality has been limited or non-existent.

SUMMARY

One aspect of the present disclosure relates to a method for generating, with one or more sensors, output signals conveying information related to one or more breathing parameters of the subject during a respiratory therapy session; determining, with one or more processors, based on the output signals, one or more breathing features of individual breaths of the subject; determining, with one or more processors, a distribution of the one or more breathing features over a plurality of time windows, at least one of the time windows having a length of at least 60 seconds; determining, with one or more processors, sleep states of the subject by mapping the distribution of the breathing features to one or more sleep states using a sleep stage classifier model configured to determine the sleep states; and providing, with one or more processors, feedback indicating the sleep states during the respiratory sleep session.

Another aspect of the present disclosure relates to a method comprising generating, with one or more sensors, output signals conveying information related to one or more breathing parameters of the subject during a respiratory therapy session; determining, with one or more processors, based on the output signals, one or more breathing features of individual breaths of the subject; determining, with one or more processors, a distribution of the one or more breathing features over a plurality of time windows, at least one of the time windows having a length of at least 60 seconds; determining, with one or more processors, sleep states of the subject by mapping the distribution of the breathing features to one or more sleep states using a sleep stage classifier model configured to determine the sleep states; and providing, with one or more processors, feedback indicating the sleep states during the respiratory sleep session.

Another aspect of the present disclosure relates to a sleep staging system comprising: means for sensing configured for generating output signals conveying information related to one or more breathing parameters of the subject during a respiratory therapy session; means for determining breathing features configured to determine one or more breathing features of individual breaths of the subject based on the output signals; means for determining distribution of the breathing features configured to determine a distribution of the one or more breathing features over a plurality of time windows, at least one of the time windows having a length of at least 60 seconds; means for determining sleep states configured to determine sleep states of the subject by mapping the distribution of the breathing features to one or more sleep states using a sleep stage classifier model configured to determine the sleep states; and means for providing feedback configured to provide feedback indicating the sleep states during the respiratory sleep session. [01]

In another aspect of the present disclosure relate to a system configured to classify sleep stages for a subject during a respiratory therapy session with a CPAP device. The system comprises a CPAP device configured to provide a respiratory therapy to a subject. The CPAP device comprises a pressure generator configured to generate a pressurized flow of breathable gas for delivery to the airway of a subject based on a respiratory therapy. The CPAP device comprises one or more sensors configured to generate output signals conveying information related to one or more breathing parameters of subject during a respiratory therapy session. The system comprises one or more physical computer processors configured by computer readable instructions to: control operations of the pressure generator to provide the respiratory therapy; determine, based on the output signals, one or more breathing features of individual breaths of the subject; determine a distribution of the one or more breathing features over one or more time windows having a length of at least 60 seconds; determine a current sleep state of the subject by mapping the distribution of the breathing features to one or more sleep states using a sleep stage classifier, the sleep stage classifier comprising one or more models configured to determine the current sleep state; and provide feedback indicating the current sleep state information.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
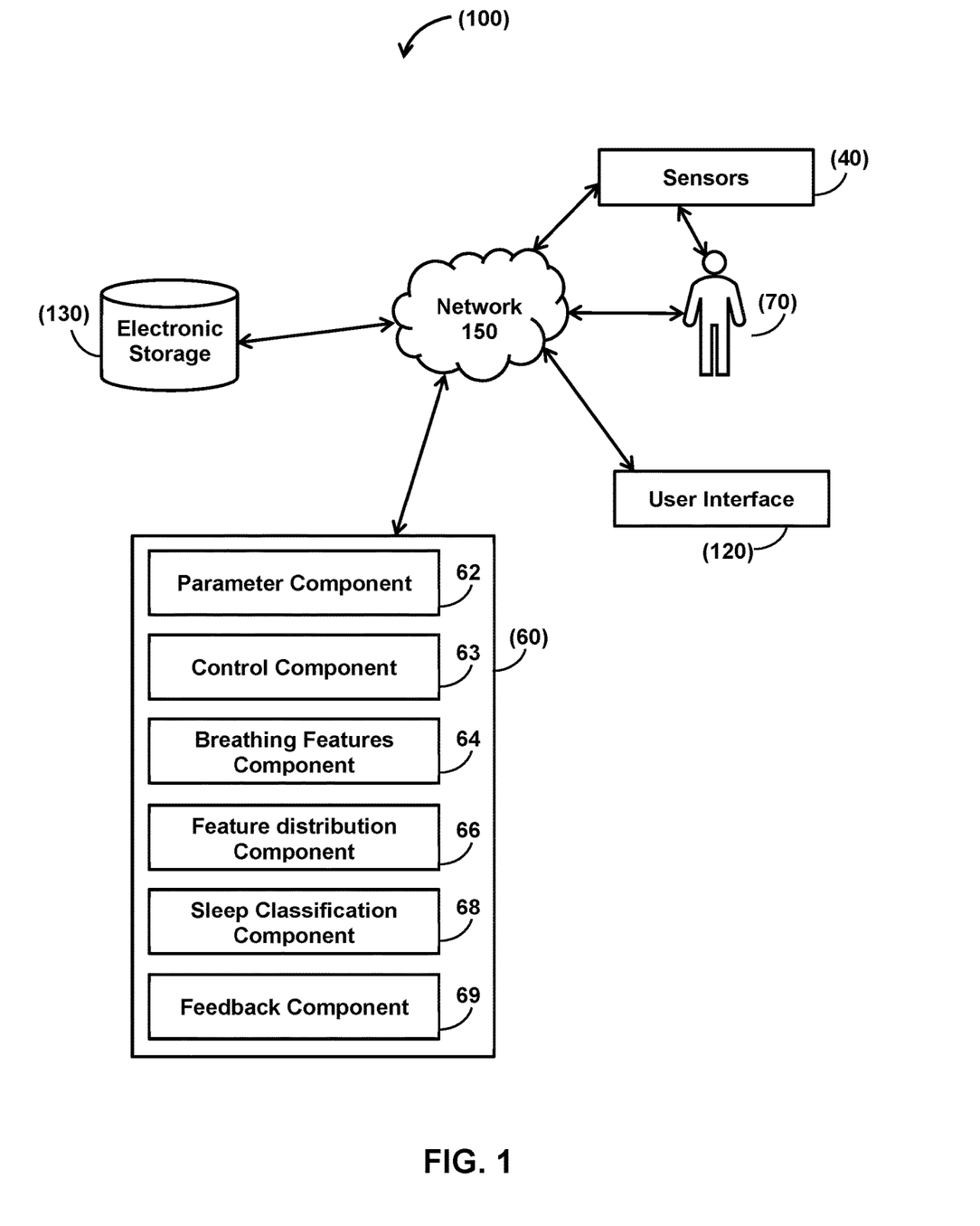
FIG. 1 illustrates a sleep staging system 100 for classifying sleep stages for a subject, according to one or more embodiments.

FIG. 1 illustrates an example of a system 100 for classifying sleep stages for a subject, according to one or more embodiments of the present disclosure. In some embodiments, system 100 is configured to determine breathing parameters of a subject. Determining the breathing parameters include detecting individual breaths of the subject. System 100 is configured to classify sleep stages of the subject based on breathing features of the individual breaths. The breathing features of each breath may include duration of the breath, duration of inspiration vs expiration of the breath, minimum and/or maximum flow of the breath, and/or tidal volume of the breath. In one embodiment, the sensors (40) to be described in detail below, can be incorporated into a device that interfaces with the subject and obtains output signals (such as those pertain to breathing (flow rate, pressure, tidal volume, etc), cardiovascular (heart rate, blood pressure, etc), and/or other physiological measurements from the subject. For example, in one embodiment, the sensors (40) can be incorporated in a CPAP machine as well be described in connection with some embodiments.

Presence of sleep events may have an impact on the sleep architecture of a subject, and/or the characteristics of features used for sleep classification. For example, if a subject is in sleep stage N3 and a central sleep apnea event occurs. central sleep apnea event may cause a change in the respiratory characteristics during the event (no breathing effort during the apnea) and in the period immediately after the event (usually breathing resumes, with higher frequency and amplitude during the hyperpnea). The central apnea event is often followed by an arousal event, which may cause a change in heart rate variability characteristics due to the burst in sympathetic activity during the arousal period. After the arousal, the subject enters a period of "lighter" sleep, typically N1 or N2. Without information about the occurrence of this breathing event, and if the cardiac or respiratory features are analyzed in a time window during which the event occurs, the classifier might be unable to detect the N3 period preceding the arousal (typically N3 is characterized by a low sympathetic tone with regular breathing amplitude and frequency). Knowing that an apnea and subsequent arousal occurred, the classifier may easily associate the characteristics of the features to the sequence of sleep stages and may easily infer what the following sleep stage will likely be. Using breath events in the determination of the sleep states provides for an improved sleep classification performance.

In some embodiments, the breathing features are first extracted, and then respiratory characteristics are analyzed using different time windows to characterize a value distribution of the features. The respiratory characteristics are analyzed with descriptive using one or more windows (lasting 30, 30, or more seconds) to characterize the value distribution of the breathing features. The size of the windows is time based (e.g. 30, 30, 90, 150 seconds, etc.), independently from the number of breaths contained in the window. In some embodiments, the statistics (meta-features) for a breathing feature describe the shape of a distribution of the feature over one or more time windows (e.g., a median, different percentiles, range, etc.) This is more advantageous than measuring variance or standard deviation of the breathing features in the analysis windows. The statistics (meta-features) are then used as input to a sleep stage classifier to classify the sleep stages of the subject during the therapy session. This step provides for a good mapping between sleep stages and measured statistics. The mapping would not be as robust (which results in a model with lower classification performance) if the sleep stages are mapped directly from breathing features. The term "mapping" as used herein should be itself broadly construed to mean determining a sleep state with the model, using the provided inputs into the model.

In some embodiments, the sleep stage classifier uses models that express the likelihood of a state happening based on the observations of that state, what happened in the preceding state, and on the history of states until then. In some cases, the sleep stage classifier uses bidirectional models, where the likelihood of a stage at a given point during the night depends on what happened before, but also what will happen after that point, until the subject finally wakes up in the morning. These models may be more advantageous than models that uses time-shifted input (e.g., Markov) in expressing the likelihood of a current state using memory (e.g., preceding state and history of states until then) to provide context to the current detection. Models with memory such as recurrent neural networks, long short term memory, or causal convolutional neural networks, are beneficial to explore the structured nature of sleep, and the changes in the likelihood that a sleep stage occurs after a given history of (detected) sleep stages during the night, until that point. For example, if more than one hour of N3 has been detected, it becomes increasingly less likely that N3 still occurs. Memory-based models can use this information to infer not only the most likely sleep stage at each point in time, but also the most likely sequence of sleep stages throughout the whole night based on what happened until that point. Optionally, and if causal staging is not required (e.g. for real-time applications) and observations from the whole night are available, bidirectional models can be used, whereby inference about the sleep stage at a given point can use information about the future, i.e. what the observations are after that point. For example, if the observations of a following state are very likely indicating the presence of a REM stage, it is very unlikely that the current stage is N3 or Wake, but more likely N1 or N2. The inclusion of BE meta-features improves the performance of a system where only breathing feature statistics (meta-features) are used and no influence of breathing events are taken into account. The idea behind this is that the occurrence of breathing events (e.g. apnea, hypopnea) influence the sleep architecture. For instance, after an apnea event, likely there will be an arousal and the most likely sleep stage will be N1 or N2. The result is that the sleep staging classifier, using the BE meta-features, can learn more about the sleep architecture, and will show better classification performances In some embodiments, system 100 comprises one or more sensors 40, one or more physical computer processors 30, a user interface 120, electronic storage 130, a network 150, and/or other components.

In some embodiments, sensor(s) 40 are configured to generate output signals conveying information related to one or more breathing parameters of subject 70. In some embodiments, the one or more breathing parameters may comprise gas parameters related to pressurized flow of breathable gas provided by device for providing respiratory therapy to the subject (e.g., PAP machine) breathing parameters related to respiration of subject 70, physiological parameters of subject 70, and/or other parameters. The one or more gas parameters of the pressurized flow of breathable gas may comprise, for example, one or more of a flow rate, volume, pressure, humidity, temperature, acceleration, velocity, and/or other parameters of the breathable gas. Breathing parameters related to the respiration of subject 70 may comprise a tidal volume, a timing (e.g., beginning and/or end of inhalation, beginning and/or end of exhalation, etc.), a respiration rate, a respiration airflow, a duration (e.g., of inhalation, of exhalation, of a breathing cycle, etc.), respiration frequency, effort of breathing, and/or other breathing parameters. Physiological parameters may include oximetry parameters, pulse, temperature, blood pressure, and/or other physiological parameters. In one embodiment, the breathing features detected by the one or more sensors may also include "breathing features" of individual breaths of the subject as will be described later.

In some embodiments, various types of sensor(s) 40 can be used. In various embodiments, such sensors will be or include one or more one or more non EEG type sensors (configured to generate non-EEG signals). For example, sensor(s)40 may be one or more PPG sensor(s) that generate photoplethysmogram (PPG) signals. PPG is an optically obtained plethysmogram that can be used to detect blood volume changes in the microvascular bed of tissue, changes in chest and/or abdominal volume. A PPG may be obtained by using a pulse oximeter, belts around patient's chest and abdomen. In some embodiments, sensor(s) 40 may be one or more ECG sensor(s) that generate electrocardiography signal. An electrocardiogram (ECG) is a recording of the electrical activity of the heart. An ECG may be obtained using electrodes placed on the skin of the patient. In some embodiments, sensor(s)40 may be one ore more BCG sensors that generate a ballistocardiograph (BCG) signal. A BCG signal is a graphical representation of repetitive motions of the human body arising from the sudden ejection of blood into the great vessels with each heartbeat. BCG can be obtained using noninvasive methods (e.g., from sensors on the surface of the body, or using a sensor in the form of a camera in a non-contact manner. In some embodiments, sensor(s) 40 may be configured for tracking movement of a chest/abdomen marker by using an infrared camera to measure respiratory effort of the subject. In some embodiments, PPG, ECG, and/or BCG may be used to determine the subjects respiratory effort.

Sensor(s)40 may comprise one or more sensors that measure such parameters directly (e.g., through fluid communication with the subject, a subject interface, a respiratory therapy device, etc.) In some embodiments, sensor(s) 40 may comprise one or more sensors that generate output signals related to the one or more parameters indirectly. For example, sensor(s) 40 may comprise one or more sensors configured to generate an output based on an operating parameter of a respiratory therapy device (e.g., subject flow and/or pressure estimations from motor current, voltage, rotational velocity, and/or other operating parameters), and/or other sensors. In some embodiments, sensor(s) 40 may include one or more of flow, position, volume, pressure, humidity, temperature, heart, motion, acceleration, oximetry, audio, video, photo sensors, and/or other sensors. Sensor(s) 40 may comprise sensors disposed in a plurality of locations, such as for example, at various locations within (or in communication with) subject interface, on subject 70, within (or in communication with) a respiratory therapy device, a conduit 50, and/or other locations.

Processor(s) 30 is configured to provide information processing capabilities in system 100. As such, processor(s) 30 may include one or more digital processors, one or more analog processor, one or more digital circuits designed to process information, one or more analog circuits designed to process information, a state machine, and/or other mechanisms for electronically processing information. In some embodiments, processor(s) is operatively connected to sensors (40). Although processor(s) 30 is shown in FIG. 1 as a single entity, this is for illustrative purposes only. In some implementations, processor(s) 30 includes a plurality of processing units. These processing units may be physically located within the same device (e.g., sensors(40) or a device that includes sensors (40)), or processor(s) 30 may represent processing functionality of a plurality of devices operating in coordination and located outside of system 100 (e.g., in the Cloud). In some embodiments, processors (30) may represent processing functionality of a plurality of devices located within and/or outside system 100 (e.g., communicatively coupled via a network 150).

As shown in FIG. 1, processor(s) 30 is configured to execute one or more computer program components. The one or more computer program components may comprise one or more of a parameter component 32, a control component 33, a breathing feature determination component 34, a feature distribution component 33, a sleep classification component 38, a feedback component 39, and/or other components. Processor(s) 30 may be configured to execute components 32, 33, 34, 33, 38 and 39 by software; hardware; firmware; some combination of software, hardware, and/or firmware; and/or other mechanisms for configuring processing capabilities on Processor(s) 30.

It should be appreciated that although components 32, 33, 34, 33, 38 and 39 are illustrated in FIG. 1 as being co-located within a single processing unit, in implementations in which Processor(s) 30 comprises multiple processing units, one or more of components 32, 33, 34, 33, 38 and 39 may be located remotely from the other components. The description of the functionality provided by the different components 32, 33, 34, 33, 38 and 39 described below is for illustrative purposes, and is not intended to be limiting, as any of components 32, 33, 34, 33, 38 and 39 may provide more or less functionality than is described. For example, one or more of components 32, 33, 34, 33, 38 and 39 may be eliminated, and some or all of its functionality may be provided by other components 32, 33, 34, 33, 38 and/or 39. As another example, Processor(s) 30 may be configured to execute one or more additional components that may perform some or all of the functionality attributed below to one of components 32, 34, 33, 38 and/or 39.

Parameter component 32 may be configured to receive, determine and/or obtain one or more parameters within system 100. For example, the one or more parameters may be determined based on the output signals from sensor(s) 40. In some embodiments, parameter component 32 is configured to determine one or more breathing parameters related to respiration of subject 70, one or more parameters of a breathable gas within system 100, (e.g., parameters related to pressurized flow of breathable gas delivered by a respiratory therapy device), one or more physiological parameters of subject 70, and/or other parameters. The breathing parameters related to the respiration of subject 70 may comprise beginning and/or end of individual breaths. In some embodiments, the breathing parameters may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiratory airflow, breathing effort, respiration frequency, AHI index (apnea and hypopnea index) and/or other breathing parameters. The one or more gas parameters of the pressurized flow of breathable gas may comprise, for example, one or more of a flow rate, heart rate, volume, pressure, humidity, temperature, acceleration, velocity, and/or other gas parameter. Physiological parameters may include oximetry parameters, a pulse, temperature, blood pressure, movement, and/or other physiological parameters.

In some embodiments, parameter component 32 may be configured to detect breathing events experienced by the subject. Such breathing events may include events that disrupt respiration by subject 70. In some embodiments, parameter component may be configured to detect disruptions of the respiration of subject indicative of presence of respiratory events. For example, such breathing events may include one or more of obstructive apneas, central apneas, glottal closures, Cheyne-Stokes respiration, hypopnea, snoring, hyperventilation, arousal, and/or other breathing events. and/or other respiratory events. Parameter component 32 detects such breathing events based on the output signals generated by sensors 40. For example, by monitoring one or more of flow rate, pressure, respiratory airflow, breathing effort, instantaneous tidal volume, and/or other gas parameters at or near the airway of subject 70 (e.g., within a subject interface).

Control component 33, in some embodiments, is configured to control operations of sensors (40). For example, in some embodiments control component may be configured to activate/deactivate the one or more sensors based on user input, measurement results, on a request from one or more components within or outside of system 100.

Figure 2:
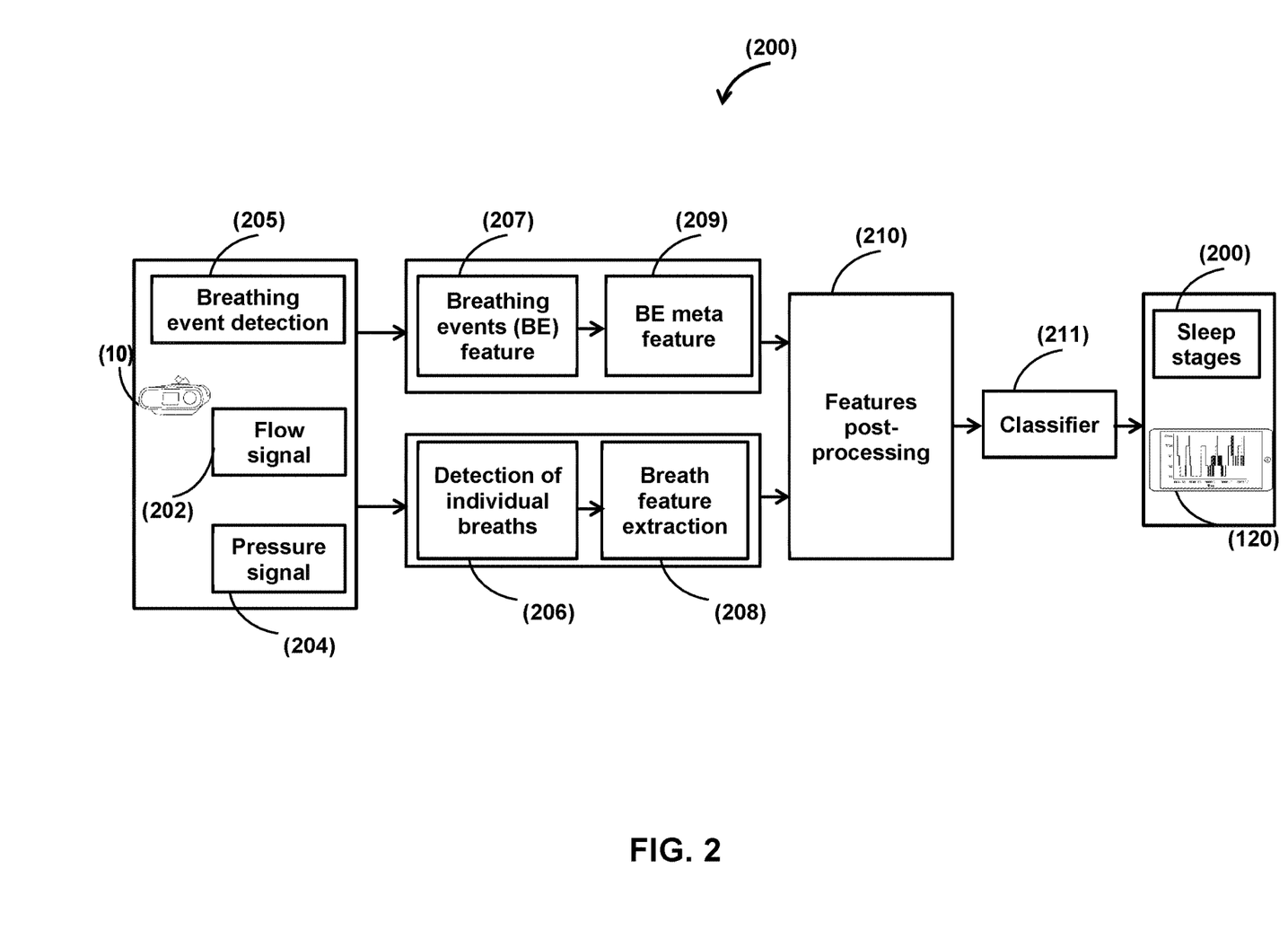
FIG. 2 illustrates an example 200 of a sleep staging system 200 for classifying sleep stages for a subject, according to one or more embodiments.

Breathing feature determination component 34, is configured to determine one or more breathing features of individual breaths of the subject. In some embodiments, each breath can be characterized by more than one breathing feature. For example, the breath duration, the duration of inspiration vs expiration, minimum and maximum flow rate values, tidal volume, etc. In some embodiments, one or more breathing features may vary depending on the sleep stage of the subject. For example, during N3, breathing becomes slower, and more regular, both in terms of amplitude as well as in terms of frequency. In some embodiments, system 200 comprises computer processors configured to detect individual breaths 203 of the subject based on the output signals. the output signals are non-EEG signals (e.g. ECG, PPG, BCG, respiratory effort, etc.). In some embodiments, each breath is then characterized in terms of several of its signal properties. For example, describing its duration, the duration of inspiration vs expiration, minimum and maximum flow values, tidal volume, etc. The breath features 208 are post-processed 210 and adopted by a pre-trained machine learning model 211, with memory, to automatically classify sleep stages 212 in pre-defined epochs of 30 seconds based on those features. In some embodiments, this information is then fed back to the user in the form of a feedback indicating the sleep state. for example, system 200 may be configured to display the determined sleep stage 212. For example, the display may be user interface (described above), an app on his/her smartphone 120, etc.

Figure 3:
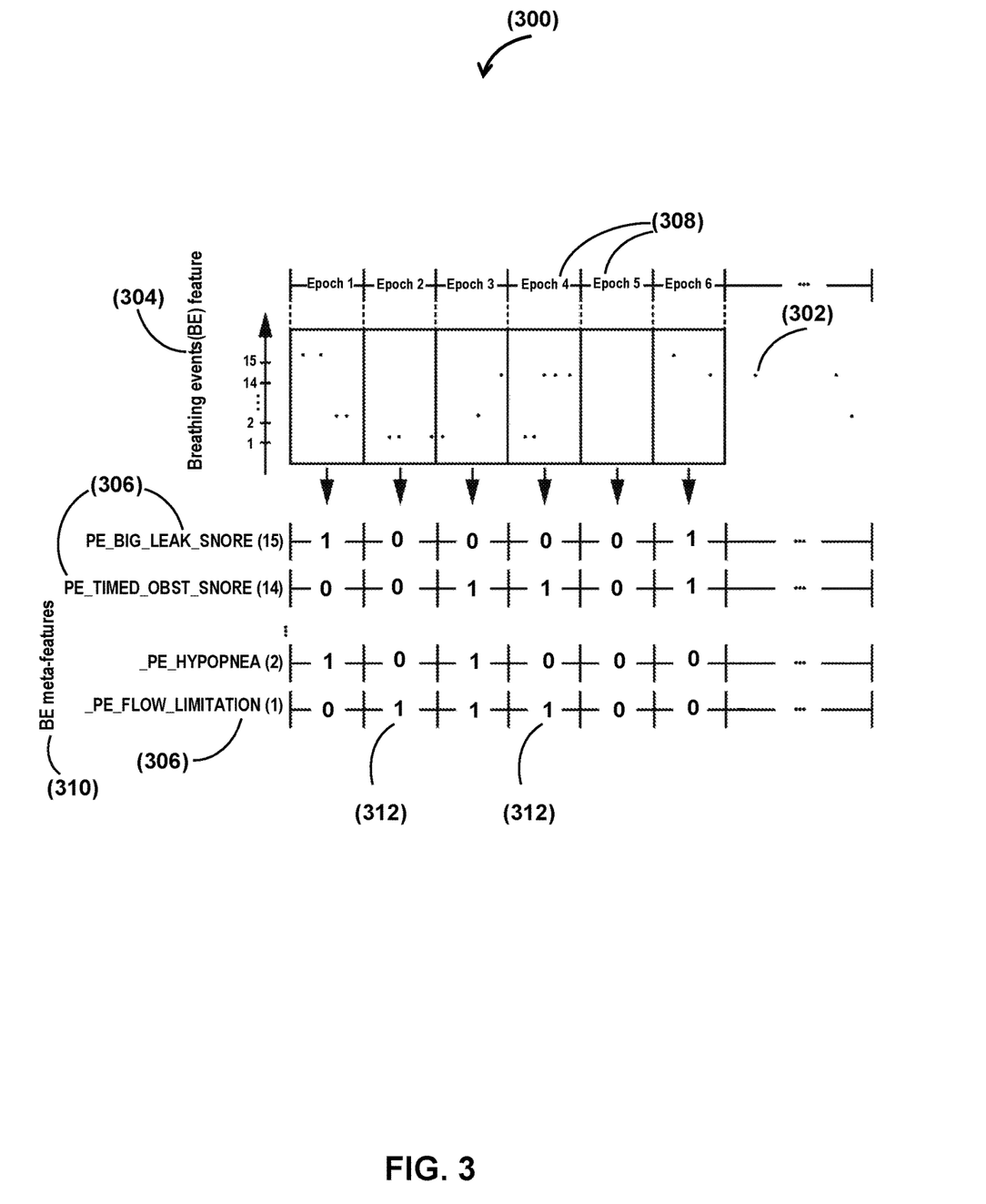
FIG. 3 illustrates an example 300 of a windowing process, according to one or more embodiments.

In some embodiments, the (BE) feature values 207 (numeric values) are used to indicate the category of a detected event 205. This process is illustrated in FIG. 3. FIG. 3 illustrates an example 300 of a windowing process used to determine the distribution of a given BE feature 302 over time, according to one or more embodiments.

FIG. 3 describes a distribution 302 of breathing event (BE) feature 304 over time. The Y axis of the distribution represents the breathing event (BE) feature values 304. The X axis of the distribution represents time centered on 30-second epochs 308, is used in characterization the (BE) feature over the time window 308. FIG. 3 shows that 15 new meta-features 306 are created, indicating, for each epoch, whether the corresponding event was detected (as indicated by the BE feature 304) inside the window defined by the boundaries of that epoch.

For example, if for a given epoch 308, at least one event of type 2 (hypopnea) 304 was detected, then the corresponding feature 306 (_PE_HYPOPNEA) will have a value of 1 for that epoch. If no events of type 2 were detected for a given epoch, then the feature will have a value of 0. Note that this is the case even if multiple events of the same type are detected in the same epoch, i.e., each epoch will have a flag value of 0 or 1, meaning that one or more events of that type were detected. If multiple events of different types are detected in the same epoch, then all corresponding features will have a flag of 1. This is the case for example, in the first epoch of the example illustrated in FIG. 3 where events 304 of type 2 and 15 were detected in the same epoch. In this case, features 306_PE_HYPOPNEA (2) and _PE_BIG_LEAK_SNORE (15) both get a flag of 1 for the first epoch, whereas all other features get a flag of 0.

Feature distribution component 36, is configured to determine/describe a distribution of the one or more breathing features over one or more-time windows. In some embodiments, feature distribution component 36 describes the shape of the distribution of the breathing feature over time. For example, a median, different percentiles, range, and/or other description (e.g., characteristics) of the shape of the distribution adequate to characterize the properties of the breath feature over the time windows. In some embodiments, the time windows have a length of at least 30 seconds each. For example, the time windows may have 30, 90, 120, 150 seconds, or other lengths. In some embodiments, the length of time windows may be first estimated based on a known behavior of sleep. Longer windows (e.g., longer than 30 seconds usually used in sleep stages annotated with polysomnography) are more advantageous in characterizing the breathing features in a way that is correlated with the occurrence of different sleep stages. For example, during N3 longer windows may be better in characterizing the breathing features because breathing becomes slower, and more regular. In some embodiments, feature distribution component 36, is configured to determine distribution of the one or more breathing features over one or more-time windows having different sizes (different length). For example, brief awakenings occurring during the night, often lasting less than one or two minutes, are associated with abrupt changes in breathing patterns and breathing frequency. A combination of breath feature statistics, (meta-features) captured with different window sizes, will allow a proper separation of sleep stages with distinct time and frequency patterns. For example, the sleep state N3 is characterized by longer periods of breathing stability, where for example, Awake is characterized by short transient activity. Sleep is scored within 30 second epochs, so makes sense to use multiples of 30 for window sizes. Through a training process (for the classifier) that accounts for meta-features from all window lengths, an optimal set of meta-features, and thus, an optimal set of window sizes is determined.

Sleep staging component 38 is configured to determine a current sleep state of the subject. For example, wake, N1, N2, N3, REM or combination of these states (e.g., wake, N1+N2, N3, REM). In some embodiments the current sleep state is determined by mapping the distribution of the breathing features to one or more sleep states using a sleep stage classifier. In some embodiments, the sleep stage classifier comprises one or more models configured to determine the current sleep state. In some embodiments, using a selected number of breath feature statistics(meta-features), machine learning models can be used to map parts of the feature space to given sleep stages (wake, N1, N2, N3, REM) or combination of these (most commonly wake, N1+N2, N3, REM). This classification process is performed separately on each of the 30-second epochs, to obtain as a result, a categorical classification of each epoch according to which sleep stage it is more likely to have occurred there. In some embodiments, sleep state models may be trained with inputs (e.g., meta-features) and answers (e.g., the sleep stage). Once trained (with inputs and corresponding answers) the models are ready to be used. In some embodiments, in operation, the sleep state model receives input (e.g., meta-feature) and uses the stored relationships to give its prediction of sleep stage based on how it had been trained. In some embodiments, a bidirectional model that uses information from the past and future may be used. In some embodiments, an unidirectional or causal model that only has information from the past may be used.

In some embodiments, the one or more models are configured to determine the current sleep state based on a plurality of sleep states directly preceding the current state. In some embodiments, the sleep stage classifier uses models that express the likelihood of a state happening based on the observations of that state, what happened in the preceding state, and on the history of states until then. In some cases, the sleep stage classifier uses bidirectional models, where the likelihood of a stage at a given point during the night depends on what happened before, but also what will happen after that point, until the subject finally wakes up in the morning. These models may be more advantageous than models that uses time-shifted input (e.g., Markov) in expressing the likelihood of a current state using memory (e.g., preceding state and history of states until then) to provide context to the current detection.

Models with memory such as recurrent neural networks, long short term memory, or causal convolutional neural networks, are beneficial to explore the structured nature of sleep, and the changes in the likelihood that a sleep stage occurs after a given history of (detected) sleep stages during the night, until that point. For example, if more than one hour of N3 has been detected, it becomes increasingly less likely that N3 still occurs. Memory-based models can use this information to infer not only the most likely sleep stage at each point in time, but also the most likely sequence of sleep stages throughout the whole night based on what happened until that point.

In some embodiments, where causal staging is not required (e.g., for non real-time applications) and observations from the whole night are available, bidirectional models can be used, whereby inference about the sleep stage at a given point can use information about the future, i.e. what the observations are after that point. For example, if the observations of a following state are very likely indicating the presence of a REM stage, it is very unlikely that the current stage is N3 or Wake, but more likely N1 or N2.

Feedback component 39 is configured to provide feedback indicating the current sleep state information. In some embodiments, for sleep stages detected for a full- or partial-night recording, feedback can be given to the user regarding the progression of sleep stages throughout his/her sleep, regarding some statistics, such as the number of minutes (or percentage) in import sleep stages such as N3 or REM, the number of awakenings during the night, the sleep efficiency (percentage of time asleep versus amount of time in bed), etc. In some embodiments, some of the measured sleep statistics (meta-features)can be combined in a single sleep score quantifying the "quality" of the user's sleep, for example using a weighted average of these sleep statistics, normalized by the person's age. In some embodiments, feedback on the user interface on the CPAP machine, a smart phone, etc.

User interface 120 is configured to provide an interface between system 100 and subject 70 and/or other users through which subject 70 and/or other users may provide information to and receive information from system 100. Other users may comprise, for example, a caregiver, a doctor, and/or other users. This enables data, cues, results, and/or instructions and any other communicable items, collectively referred to as "information," to be communicated between a user (e.g., subject 70) and one or more of pressure generator 20, Processor(s) 30, and/or other components of system 100. As another example, sleep stages, sleep duration, breathing feature distribution, therapy information feedback, the breath rate of subject 70, and/or other information may be displayed to a user (e.g., subject 70) via user interface 120. Examples of interface devices suitable for inclusion in user interface 120 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 120 comprises a plurality of separate interfaces.

It is to be understood that other communication techniques, either hard-wired or wireless, are also contemplated by the present disclosure as user interface 120. For example, the present disclosure contemplates that user interface 120 may be integrated with a removable storage interface provided by electronic storage 130. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 120 comprise, but are not limited to, an RS-232 port, RF link, an IR link, modem (telephone, cable or other). In short, any technique for communicating information with system 100 is contemplated by the present disclosure as user interface 120.

In some embodiments, electronic storage 130 comprises electronic storage media that electronically stores information. The electronic storage media of electronic storage 130 may comprise one or both of system storage that is provided integrally (i.e., substantially non-removable) with system 100 and/or removable storage that is removably connectable to system 100 via, for example, a port (e.g., a USB port, a firewire port, etc.) or a drive (e.g., a disk drive, etc.). Electronic storage 130 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 may store software algorithms, information determined by Processor(s) 30, information received via user interface 120, and/or other information that enables system 100 to function properly. Electronic storage 130 may be (in whole or in part) a separate component within system 100, or electronic storage 130 may be provided (in whole or in part) integrally with one or more other components of system 100 (e.g., user interface 120, Processor(s) 30, etc.)

Network 150 may include the Internet and/or other networks, Intranets, a PAN (Personal Area Network), a LAN (Local Area Network), a WAN (Wide Area Network), a SAN (Storage Area Network), a MAN (Metropolitan Area Network), near field communication, frequency (RF) link, Bluetooth, Wi-Fi, Li-FI, a cellular communications network, a Public Switched Telephone Network, and/or any type(s) of wired or wireless network(s). It will be appreciated that this is not intended to be limiting and that the scope of this disclosure includes embodiments in which the components of system 100 are operatively linked via some other communication media. In some cases, the network is a secure local area network, such as a wired Ethernet network behind a firewall.

Information determined by Processor(s) 30 and/or stored by electronic storage 130 may comprise information related to sensor measurements, respiration of subject 70, sleep states, feedback, and/or other information. The information stored by electronic storage 130 may be viewed via user interface 120, by connecting (wired and/or wireless) to a separate computer, and/or other via other methods. The information stored by electronic storage 130 may be used, for example, to adjust therapy settings, used by a doctor to make medical decisions, and/or for other uses. In some embodiments, system 100 may include a wireless transmitter (not shown) and the information determined by Processor(s) 30, the information stored by electronic storage 130, and/or other information may be communicated to a caregiver, for example, over a wireless network. By way of a non-limiting example, the caregiver may receive use information, subject status, and/or other information, allowing the caregiver to remotely track the therapy delivered by system 100.

In some embodiments, processing functionality of system 100, described herein, is accomplished locally in a therapy device (e.g., a sensor, a respirator therapy device, etc.) that includes the components of system 100 described above. In some embodiments, processing functionality of system 100 described herein is accomplished outside of system 100 (e.g., remotely by one or more devices connected to system 100 via network 100.) I some embodiments, the processing functionality described herein, may be a combination of processing functionality executed locally and processing functionality executed remotely.

Figure 4:
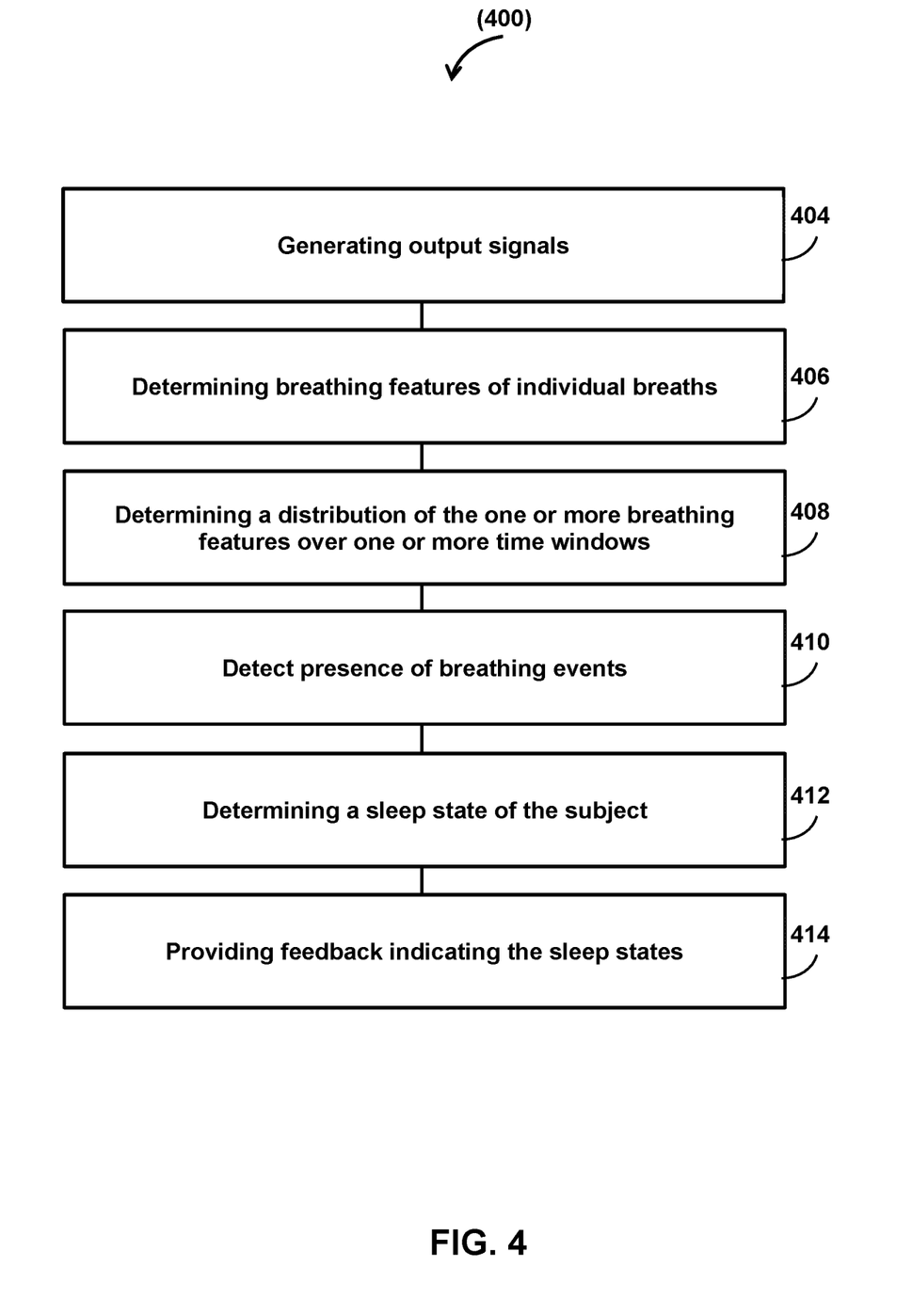
FIG. 4 illustrates a method 400 for classifying sleep stages for a subject, according to one or more embodiments.

FIG. 4 illustrates a method 400 for using breathing events in classifying sleep stages for a subject, during a respiratory therapy session with a CPAP device. The operations of method 700 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 404, output signals conveying information related to one or more breathing parameters of the subject are generated. In some embodiments, operation 404 is performed by one or more sensors the same as or similar to sensor(s) 40 (shown in FIG. 1 and described herein).

At an operation 406, one or more breathing features of individual breaths of the subject are determined based on the output signals. In some embodiments, operation 406 is performed by a physical computer processor the same as or similar to Processor(s) 60 (shown in FIG. 1 and described herein).

At operation 408, a distribution of the one or more breathing features over one or more time windows is determined. In some embodiments, operation 406 is performed by a physical computer processor the same as or similar to Processor(s) 60 (shown in FIG. 1 and described herein).

At an operation 410, one or more breathing events are detected based on the output signals. In some embodiments, operation 410 is performed by a physical computer processor the same as or similar to Processor(s) 60 (shown in FIG. 1 and described herein).

At an operation 412, a sleep state of the subject is determined. based upon the distribution of the breathing features and the one or more breathing events. In some embodiments, operation 412 is performed by a physical computer processor the same as or similar to Processor(s) 60 (shown in FIG. 1 and described herein).

At an operation 414 feedback indicating the current sleep state information is provided. In some embodiments, operation 414 is performed by a physical computer processor the same as or similar to Processor(s) 60 (shown in FIG. 1 and described herein).

The system and methods of the present disclosure may provide users of CPAP therapy an objective feedback about their sleep. This feedback maybe used, for example in a coaching app, to improve their education about sleep in general, and the benefits of sleeping with CPAP machine in their specific case, potentially helping to drive up compliance.

Figure 6A:
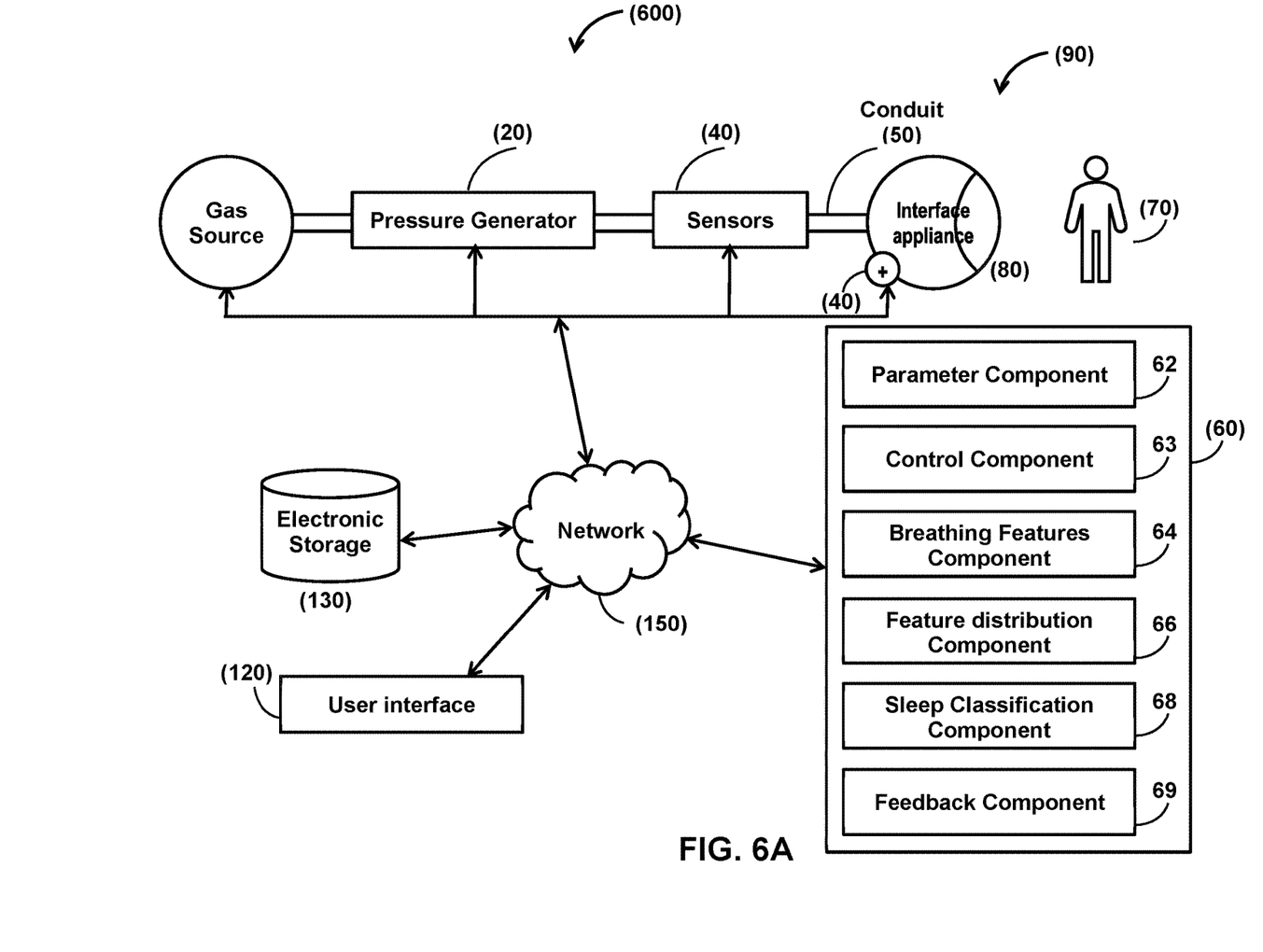
FIGS. 6A-6B illustrate examples 600 for classifying sleep stages for a subject during a respiratory therapy session with a CPAP device, according to one or more embodiments.

FIG. 6A illustrates a system 600 for classifying sleep stages for a subject during a respiratory therapy session with a CPAP device 10, according to one or more embodiments. In some embodiments, system 600 is configured to determine breathing parameters of a subject during a respiratory therapy session provided with the CPAP device 10. Determining the breathing parameters include detecting individual breaths of the subject. System 600 is configured to classify sleep stages of the subject during the therapy session based on breathing features of the individual breaths. In some embodiments, CPAP device comprises one or more of a pressure generator 20, one or more sensors 40 (described in relation to FIG. 1 above), a subject interface 90, one or more physical computer processors 60 (described in relation to FIG. 1 above), a user interface 120 (described in relation to FIG. 1 above), electronic storage 130 (described in relation to FIG. 1 above), a network 150 (described in relation to FIG. 1 above), and/or other components.

"Respiratory therapy" as meant herein is a session or period of time during which the CPAP device is being used by a subject to treat OSA. The therapy typically involves providing positive airway pressure to the subject in accordance with a software program or algorithm that is controlled by one or more processors (e.g., processors 60 described below). In some embodiments, "Respiratory therapy" as meant herein is a breathable gas therapy (e.g., Oxygen, or other breathable gas therapy). In one or more embodiments, the CPAP device, sensors, pressure generator and one or more processors may be constructed in accordance with the teachings of U.S. Pat. No. 7,168,429B2, hereby incorporated by reference in their entirety.

In some embodiments, pressure generator 20 is configured to generate a pressurized flow of gas for delivery to the airway of a subject 70. Pressure generator 20 may control one or more parameters of the flow of gas (e.g., flow rate, pressure, volume, temperature, gas composition, etc.) for therapeutic purposes, and/or for other purposes. By way of a non-limiting example, pressure generator 20 may be configured to control the flow rate and/or pressure of the flow of gas to provide pressure support to the airway of subject 70.

In some embodiments, pressure generator 20 receives a supply of breathable gas from a gas source and elevates the pressure of that gas for delivery to the airway of a subject. Pressure generator 20 may include any device, such as a pump, blower, piston, or bellows that is capable of elevating the pressure of the received breathable gas from the gas source for delivery to the subject. For example, in some embodiments pressure generator 20 may be a blower that is driven at a constant speed during the course of a pressure support treatment to produce a constant pressure or flow rate. In some embodiments, pressure generator 20 may include one or more valves for controlling the pressure, flow rate, flow direction, and/or other parameters of the flow of gas. The present disclosure contemplates controlling the operating speed of the blower, for example, either alone or in combination with one or more valves and/or other devices contained in and/or external to pressure generator 20, to control the pressure and/or flow of gas provided to subject 70.

The gas source may be atmospheric air drawn into the system by pressure generator 20. In some embodiments, the gas source may comprise a tank of pressurized gas (such as oxygen, air, or other mixture of breathable gas) in fluid communication with pressure generator 20. In some cases, a separate gas source need not be used, but instead the pressure generator 20 may itself be defined by a canister or tank of pressurized gas, with the pressure delivered to the patient being controlled by a pressure regulator.

Subject interface 90 is configured to communicate the pressurized flow of breathable gas to the airway of subject 70. As such, in some embodiments, subject interface 90 comprises conduit 50, interface appliance 80, and/or other components. In some embodiments, conduit 50 is configured to convey the pressurized flow of gas to interface appliance 80. Interface appliance 80 is configured to deliver the flow of gas to the airway of subject 70. In some embodiments, interface appliance 80 is configured to be non-invasively engaged by subject 70. Non-invasive engagement comprises removably engaging one or more external orifices of the airway of subject 70 (e.g., nostrils and/or mouth) to communicate gas between the airway of subject 70 and interface appliance 80. In some embodiments, interface appliance 80 is removably coupled to conduit 50. Interface appliance 80 may be removed for cleaning and/or for other purposes. In some embodiments, conduit 50 is configured as a mouthpiece to be engaged by the mouth of subject 70.

In some embodiments, other interface appliances may be configured as interface appliance 80. Some examples of interface appliance 80 may comprise, for example, a nasal cannula, a nasal mask, a nasal/oral mask, a full-face mask, a total face mask, or other interface appliances that communicate a flow of gas with an airway of a subject. The present disclosure is not limited to these examples and contemplates delivery of the flow of gas to the subject using any interface appliance. For example, an endotracheal tube, a tracheotomy tube, a laryngeal mask airway, and/or other invasive interface appliances.

In some embodiments, control component 33 (described in relation to FIG. 1 above) is configured to control operations of CPAP device 10. For example, in some embodiments, control component 33 is configured to control the pressure generator 20 to generate the flow of gas in accordance with one or more therapy regimes (positive pressure support therapy regime, or other respiratory therapy). In some cases, control component 33 may be configured to control operation of pressure generator 20 based on the output signals from sensor(s) 40, based on information determined by parameter component 32, and/or based on information from one or more components within or outside of system 100. For example, in positive airway pressure support therapy the pressurized flow of gas generated by pressure generator 20 is controlled to replace and/or compliment a patient's regular breathing. Positive airway pressure support therapy may be used to maintain an open airway in a patient so that oxygen and carbon dioxide may be exchanged more easily, requiring little and/or no effort from the patient.

In some embodiments, control component 33 may control pressure generator 20 such that the pressure support provided to the subject via the flow of gas comprises continuous positive airway pressure support (CPAP), bi-level positive airway pressure support (BPAP), proportional positive airway pressure support (PPAP), forced oscillation technique, and/or other types of pressure support therapy. CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation. In some therapy modes (e.g., PPAP), control component 33 may control pressure generator 20 to apply variable pressure support in which the amount of pressure delivered to the patient during inhalation and/or during exhalation is determined and delivered on a breath by breath basis. In some embodiments, control component 33 may be configured to control pressure generator 20 to temporarily drop the supplied pressure during exhalation (C-Flex) to reduce exhalation effort required by the patent.

In some embodiments, control component 33 is configured to control pressure generator 20 to deliver staged pressure support. In staged pressure support therapy, the pressure delivered by pressure generator 20 gradually increases over time. In some embodiments, control component 33 may control pressure generator 20 to switch therapy modes based on information related to the respiration of subject 70 and/or other information. For example, control component 33 may control pressure generator 20 to change from BPAP to CPAP after a certain number of breaths by subject 70

Figure 5:
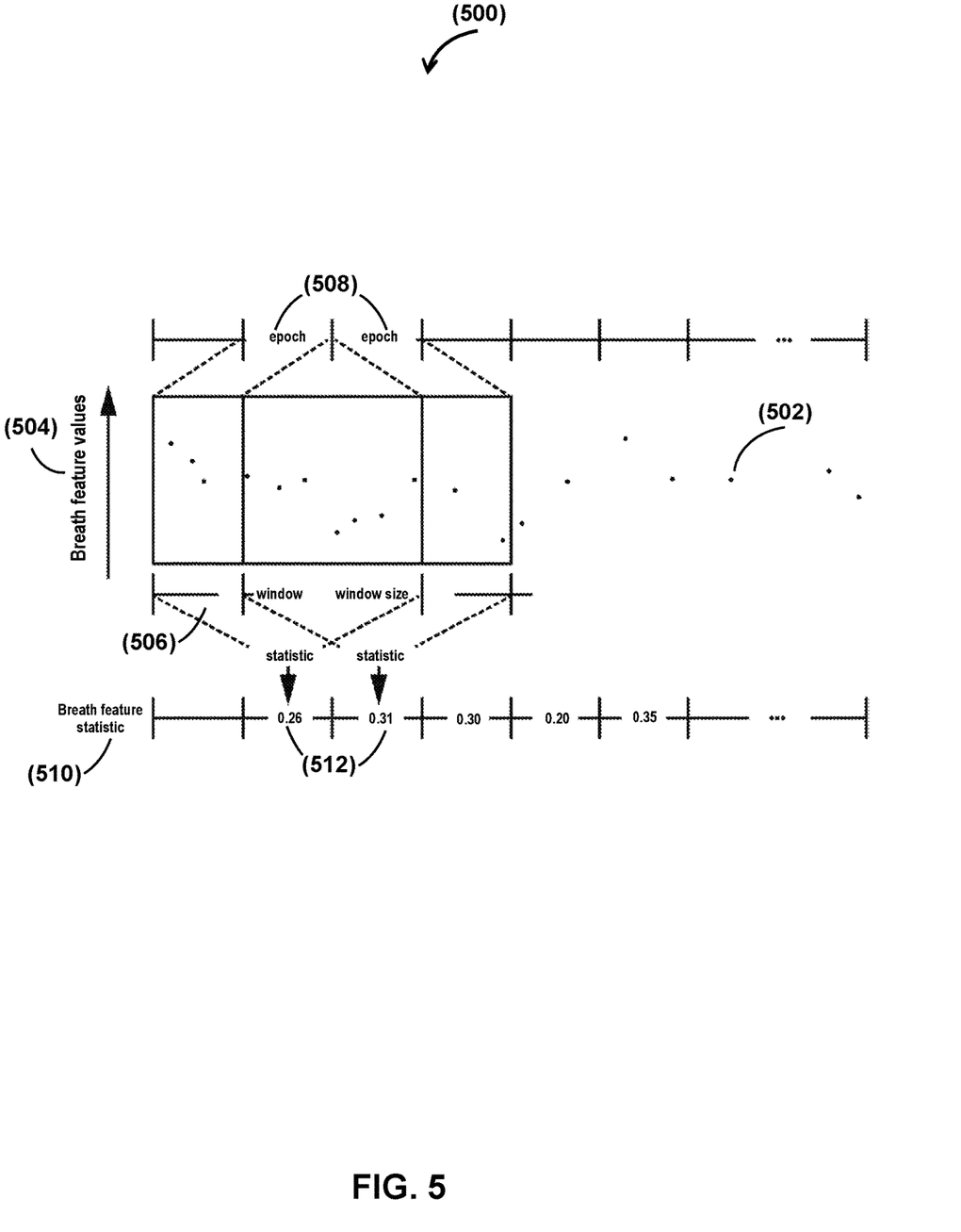
FIG. 5 illustrates of a windowing process 500 used to determine distribution of a given breathing event feature over time, according to one or more embodiments.

FIG. 5 illustrates an example 500 of a windowing process used to determine distribution of a given breath feature over time, according to one or more embodiments. FIG. 5 describes a distribution 502 of breathing feature values 504 over time. The Y axis of the distribution represents the breathing feature values 504. For example, in some embodiments, the breathing feature may be a tidal volume of the subject. In this case, the Y axis would represent tidal volume values. The X axis of the distribution represents time. In the example of FIG. 5, a sliding window 503, centered on 30-second epochs 508, is used in characterization 510 the breathing feature over the sliding time window 503. The sliding window 503 represents the amount of time over which the breathing feature values are analyzed (or characterized). As can be seen, the sliding time window 503 has a length of at least 30s. in some examples, the length of window 503 may be of different sizes (e.g., 60, 90, 120, etc.). In some cases, the characterization 510 may be performed over a plurality of windows 503 having different sizes (lengths). The time windows 503 are independent from the number of breaths contained in the windows. This is better than prior methods where characterization of breathing features is either localized to individual breaths or performed in short sequences of breaths (e.g. five breaths) and where variability (variance or standard deviation) is measured. A number of characteristic values 512 are computed over each of the set of breathing feature values (associated, in time, with detected breaths) that occur during each window 503. It should also be noted that the location of the window relative to the current epoch can take on different positions. FIG. 5 shows the window centered around the current epoch, and thus is using data from both the past and future epochs surrounding the current epoch. In other scenarios where the desire is to implement a purely casual sleep state classifier, the windows could proceed the current epoch, and could also be inclusive of the current epoch.

In some embodiments, processing functionality of system 600, described herein, is accomplished locally in a therapy device (e.g., a CPAP device) that includes the components of system 100 described above. In some embodiments, processing functionality of system 100 described herein is accomplished outside of system 100 (e.g., remotely by one or more devices connected to system 100 via network 100.) I some embodiments, the processing functionality described herein, may be a combination of processing functionality executed locally and processing functionality executed remotely.

Figure 6B:
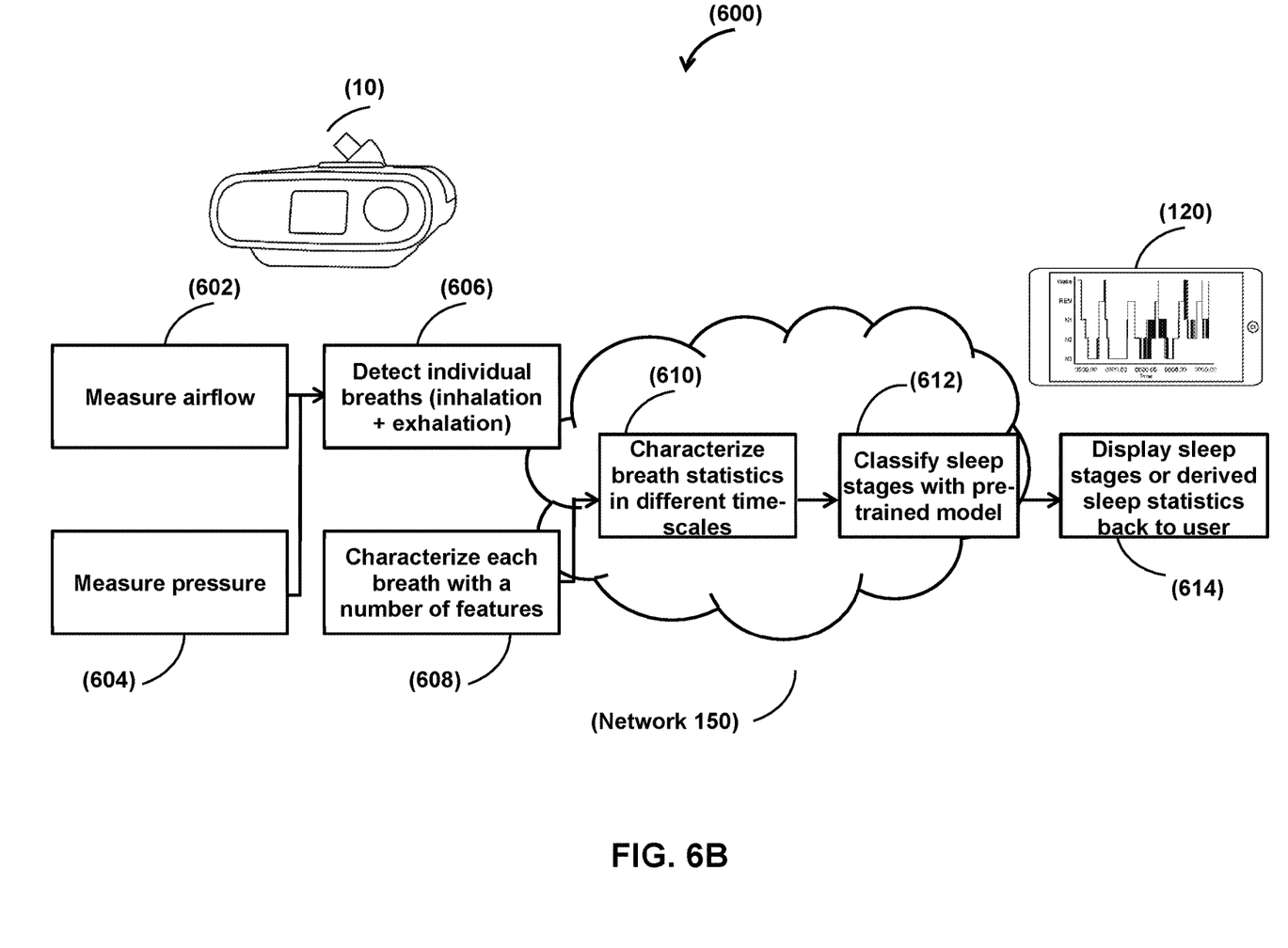

FIG. 6B illustrates an example of a system 600 for classifying sleep stages for a subject during a respiratory therapy session with a CPAP device 10, according to one or more embodiments. The system comprises a CPAP device 10 for providing respiratory therapy to the subject. The CPAP device 10 comprises the pressure generator 20 (not shown here) for generating a pressurized flow of breathable gas for delivery to the subject. System 600 comprises one or more sensors (not shown here) for generating output signals conveying information related to breathing parameters of the subject. For example, the one or more sensors may be configured to measure airflow 602, and/or pressure 604. System 600 comprises computer processors configured to detect individual breaths 603 of the subject based on the output signals. The computer processors may be configured to determine a distribution 608 of the breathing features over one or more-time windows. In some embodiments the time windows are of different length 610. The computer processors are configured to determine a current sleep state of the subject 612 by mapping the distribution of the breathing features to one or more sleep states using a sleep stage classifier. System 600 may provide 614 feedback indicating the current sleep state information. for example, system 600 may be configured to display 613 the determined sleep stage. For example, the display may be user interface described above.

Figure 7:
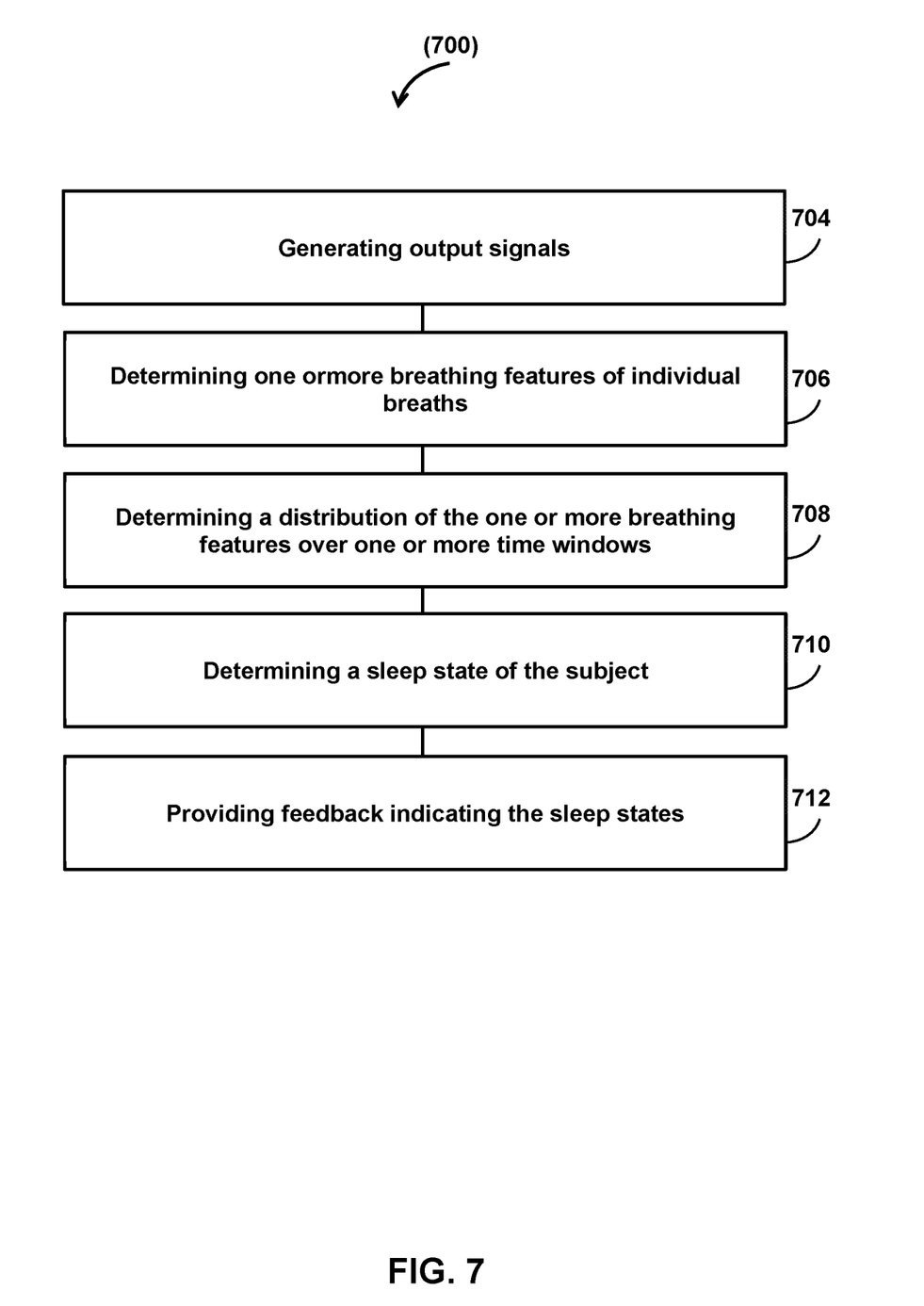
FIG. 7 illustrates a method for classifying sleep stages for a subject during a respiratory therapy session with a CPAP device, according to one or more embodiments.

FIG. 7 illustrates a method 700 for classifying sleep stages for a subject, during a respiratory therapy session with a CPAP device. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 704, output signals conveying information related to one or more breathing parameters of the subject are generated. In some embodiments, operation 704 is performed by one or more sensors the same as or similar to sensor(s) 40 (shown in FIG. 1 and described herein).

At an operation 706, one or more breathing features of individual breaths of the subject are determined based on the output signals. In some embodiments, operation 706 is performed by a physical computer processor the same as or similar to Processor(s) 60 (shown in FIG. 1 and described herein).

At an operation 708, a distribution of the one or more breathing features over one or more-time windows having a length of at least 60s each is determined. In some embodiments, operation 708 is performed by a physical computer processor the same as or similar to Processor(s) 60 (shown in FIG. 1 and described herein).

At an operation 710, a sleep state of the subject may be determined. by mapping the distribution of the breathing features to one or more sleep states using a sleep stage classifier, the sleep stage classifier comprising one or more models configured to determine the current sleep state. In some embodiments, operation 710 is performed by a physical computer processor the same as or similar to Processor(s) 60 (shown in FIG. 1 and described herein).

At an operation 712, feedback indicating the during the respiratory sleep session sleep state information is provided. In some embodiments, operation 712 is performed by a physical computer processor the same as or similar to Processor(s) 60 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A sleep staging system comprising:
   one or more sensors (40) configured to generate output signals conveying information related to one or more breathing parameters of subject during a respiratory therapy session; and
   one or more physical computer processors (60) operatively connected with the one or more sensors, the one or more physical computer processors configured by computer readable instructions to:
   determine, based on the output signals, one or more breathing features of individual breaths of the subject;
   determine a distribution of the one or more breathing features over a plurality of time windows, at least one of the time windows having a length of at least 60 seconds;
   determine sleep states of the subject by mapping the distribution of the breathing features to one or more sleep states using a sleep stage classifier model, the sleep stage classifier model configured to determine the sleep states; and
   provide feedback indicating the sleep states during the respiratory sleep session.

2. The system of claim 1, wherein the time windows are set independently from the number of breaths contained in the windows.

3. The system of claim 1, wherein the one or more breathing features of the individual breaths comprise breath duration, duration of inspiration vs expiration, minimum and maximum flow values, and/or tidal volume of each individual breath.

4. The system of claim 1, wherein the one or more physical computer processors are further configured to determine the distribution of the one or more breathing features over a plurality of windows having different lengths of time.

5. The system of claim 1, wherein the sleep classifier model is configured to determine a current sleep state based on a plurality of sleep states directly preceding the current sleep state.

6. The system of claim 5, wherein the one or more models are further configured to determine a current sleep state based on a likelihood of one or more future sleep states.

7. The system of claim 1, wherein the sleep staging system comprises a CPAP device (100), the CPAP device further comprising a pressure generator (20) configured to generate a pressurized flow of breathable gas for delivery to the airway of a subject (70), the one or more physical computer processors (60) being operatively connected with the pressure generator to control deliver of the pressurized flow of breathable gas to the airway of the subject based on the output signals from the one or more sensors.

8. A method comprising:
   generating, with one or more sensors (40), output signals conveying information related to one or more breathing parameters of the subject during a respiratory therapy session;
   determining, with one or more processors (60), based on the output signals, one or more breathing features of individual breaths of the subject;
   determining, with one or more processors (60), a distribution of the one or more breathing features over a plurality of time windows, at least one of the time windows having a length of at least 60 seconds;
   determining, with one or more processors (60), sleep states of the subject by mapping the distribution of the breathing features to one or more sleep states using a sleep stage classifier model configured to determine the sleep states; and
   providing, with one or more processors (60), feedback indicating the sleep states during the respiratory sleep session.

9. The method of claim 8, wherein the time windows are set independently from the number of breaths contained in the windows.

10. The method of claim 8, wherein the one or more breathing features of the individual breaths comprise breath duration, duration of inspiration vs expiration, minimum and maximum flow rate values, and/or tidal volume of each individual breath.

11. The method of claim 8, further comprising determining the distribution of the one or more breathing features over plurality of windows having different lengths of time.

12. The method of claim 8, wherein the sleep classifier model is configured to determine a current sleep state based on a plurality of sleep states directly preceding the current sleep state.

13. The method of claim 12, wherein the one or more models are further configured to determine a current sleep state based on the likelihood of one or more future sleep states.

14. The method of claim 8, further comprising generating a pressurized flow of breathable gas for delivery to the airway of a subject (70), the one or more physical computer processors (60) being operatively connected with the pressure generator to control deliver of the pressurized flow of breathable gas to the airway of the subject based on the output signals.

15. A sleep staging system comprising:
means for sensing (40) configured for generating output signals conveying information related to one or more breathing parameters of the subject during a respiratory therapy session;
means for determining breathing features (60) configured to determine one or more breathing features of individual breaths of the subject based on the output signals;
means for determining distribution of the breathing features (60) configured to determine a distribution of the one or more breathing features over a plurality of time windows, at least one of the time windows having a length of at least 60 seconds;
means for determining sleep states (60) configured to determine sleep states of the subject by mapping the distribution of the breathing features to one or more sleep states using a sleep stage classifier model configured to determine the sleep states; and
means for providing feedback (60) configured to provide feedback indicating the sleep states during the respiratory sleep session.

16. The system of claim 13, wherein the time windows are set independently from the number of breaths contained in the windows.

17. The system of claim 13, wherein the one or more breathing features of the individual breaths comprise breath duration, duration of inspiration vs expiration, minimum and maximum flow rate values, and/or tidal volume of each individual breath.

18. The system of claim 13, wherein the means for determining the distribution are configured to determine the distribution of the one or more breathing features over plurality of windows having different lengths of time.

19. The system of claim 13, wherein the sleep classifier model is configured to determine a current sleep state based on a plurality of sleep states directly preceding the current sleep state.

20. The system of claim 1, wherein the sleep staging system comprises a CPAP device (100), the CPAP device further comprising a pressure generating means (20) configured to generate a pressurized flow of breathable gas for delivery to the airway of a subject (70), the CPAP device comprising one or more physical computer processors (60) being operatively connected with the pressure generating means to control deliver of the pressurized flow of breathable gas to the airway of the subject based on the output signals from the sensing means.

21. The system of claim 1, wherein the one or more physical computer processors are further configured to:
detect breathing events of the subject based on the output signals; and
determine sleep states of the subject by mapping the distribution of the breathing features and the detected breathing events to one or more sleep states using a sleep stage classifier model, the sleep stage classifier model configured to determine the sleep states.

22. The method of claim 8, further comprising:
detecting breathing events of the subject based on the output signals; and
determining sleep states of the subject by mapping the distribution of the breathing features and the detected breathing events to one or more sleep states using a sleep stage classifier model, the sleep stage classifier model configured to determine the sleep states.

23. The system of claim 15, further comprising:
Detecting means (60) for detecting breathing events of the subject based on the output signals; and
Determining means (60) for determining sleep states of the subject by mapping the distribution of the breathing features and the detected breathing events to one or more sleep states using a sleep stage classifier model, the sleep stage classifier model configured to determine the sleep states.

* * * * *